United States Patent
Kirchner et al.

(10) Patent No.: US 9,791,318 B2
(45) Date of Patent: Oct. 17, 2017

(54) DISPLAY OF EFFECT COATINGS ON ELECTRONIC DISPLAY DEVICES

(75) Inventors: Eric Jacob Jan Kirchner, Leiden (NL); Roelof Johannes Baptist Gottenbos, Leiderdorp (NL); André Half, Beverwijk (NL); Ivo Bernardus Nicolaas Van Der Lans, Den Hoorn (NL)

(73) Assignee: AKZO NOBEL COATINGS INTERNATIONAL B.V., Arnheim (NL)

( * ) Notice: Subject to any disclaimer, the term of this patent is extended or adjusted under 35 U.S.C. 154(b) by 1225 days.

(21) Appl. No.: 13/265,643

(22) PCT Filed: Apr. 26, 2010

(86) PCT No.: PCT/EP2010/055523
§ 371 (c)(1),
(2), (4) Date: Jan. 3, 2012

(87) PCT Pub. No.: WO2010/125023
PCT Pub. Date: Nov. 4, 2010

(65) Prior Publication Data
US 2012/0098845 A1 Apr. 26, 2012

Related U.S. Application Data

(60) Provisional application No. 61/173,342, filed on Apr. 28, 2009.

(30) Foreign Application Priority Data

Apr. 28, 2009 (EP) ..................... 09158958

(51) Int. Cl.
*G01J 3/46* (2006.01)
*G01J 3/50* (2006.01)
(Continued)

(52) U.S. Cl.
CPC ................. *G01J 3/46* (2013.01); *G01J 3/463* (2013.01); *G01J 3/50* (2013.01); *G01J 3/504* (2013.01);
(Continued)

(58) Field of Classification Search
None
See application file for complete search history.

(56) References Cited

U.S. PATENT DOCUMENTS

| 4,813,000 A | 3/1989 | Wyman et al. |
| 2001/0036309 A1 | 11/2001 | Hirayama et al. |

(Continued)

FOREIGN PATENT DOCUMENTS

| WO | 01/25737 | 4/2001 |
| WO | 2006/030028 | 3/2006 |
| WO | 2008/121358 | 10/2008 |

OTHER PUBLICATIONS

International Search Report issued for PCT/EP2010/055523, dated Sep. 14, 2010, 6 pages.
(Continued)

*Primary Examiner* — Antonio A Caschera
(74) *Attorney, Agent, or Firm* — McDonnell Boehnen Hulbert & Berghoff LLP

(57) ABSTRACT

The invention relates to a method of displaying an image of an effect coating having texture and color properties on an electronic display device, using measured color data and measured texture data as input to generate the image, wherein the textured image is displayed with visual color properties which are maintained on a prescribed level independent of possible variations in texture properties.

18 Claims, 1 Drawing Sheet

(51) Int. Cl.
   *G06T 11/00*     (2006.01)
   *G01N 21/84*     (2006.01)
(52) U.S. Cl.
   CPC .... *G06T 11/001* (2013.01); *G01N 2021/8427* (2013.01)

(56) References Cited

U.S. PATENT DOCUMENTS

2003/0208345 A1   11/2003   O'Neill et al.
2005/0128484 A1   6/2005    Rodrigues et al.
2008/0158239 A1   7/2008    Lamy et al.

OTHER PUBLICATIONS

Kirchner, Eric, et al., "Observation of Visual Texture of Metallic and Pearlescent Materials", Color Research & Application, Aug. 2007, vol. 32, No. 4, pp. 256-266.
CIE Technical Report 175:2006, "A Framework of the Measurement of Visual Appearance", 2006, pp. 54-57.

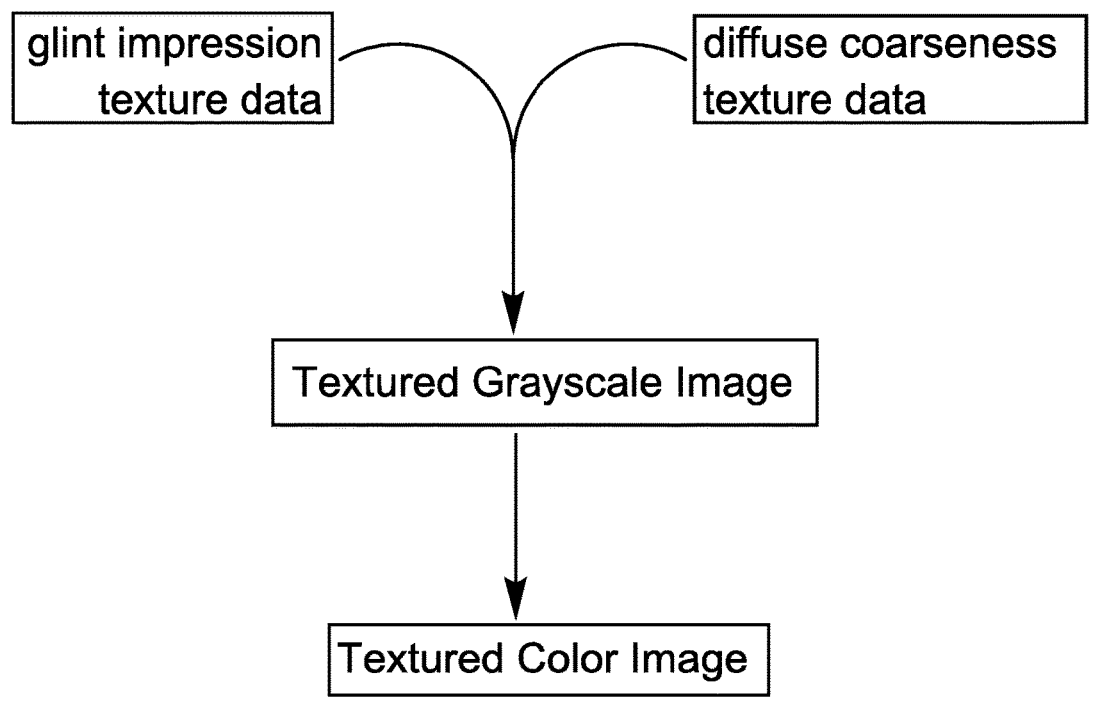

DISPLAY OF EFFECT COATINGS ON ELECTRONIC DISPLAY DEVICES

REFERENCE TO RELATED APPLICATIONS

This application is the U.S. National Phase of PCT/EP2010/055523 filed on Apr. 26, 2010, and claims the benefit of U.S. Provisional Application No. 61/173,342, filed on Apr. 28, 2009.

The invention relates to a method of displaying an image of effect coatings on electronic display devices. The invention further relates to a method of selecting a matching candidate coating, and to a system for carrying out the method.

A method of the above-mentioned type is known from International patent application WO 2008/121358. This document describes a system for digitally displaying images of various colours and appearances of an article and the use thereof. The document further describes a system for displaying images for selecting one or more formulas to match the colour and appearance of a target coating.

The values of the colour coordinates for a target colour, as measured by colour meters, actually refer to their colour as averaged over a measurement area much larger than the spatial resolution of the human eye. The spatial non-uniformity of a coloured sample is visually expressed by its texture properties.

The Commission Internationale de l'Eclairage (CIE), which is responsible for the development of international colour standards, has recognized that the perceived texture may have a great impact on the perceived difference in colour between two samples. This is stated in CIE Technical report 175:2006, A Framework for the Measurement of Visual Appearance, ISBN 3 901 906 52 5, 2006, page 55. A consequence of this effect is that when displaying the image of an effect coating, a change in the texture properties of the image will generally lead to a simultaneous change in the perceived colour properties, for example when a texture is superimposed over a coloured image.

US 2008/0158239 relates to a processor-based device for displaying simulated or modeled surface colour and surface texture data. The device may be used in conjunction with spectrophotometers, colorimeters, etc. A texture database may include information regarding surface texture and/or patterns to be modeled including automotive finishes. The device may be useful to match coatings in an auto body repair setting.

US 2005/128484 relates to a computer-implemented method for matching paint on vehicles which utilizes a video monitor display to assist the user in selecting an optimally matched colour coating. The colour characteristics of a target colour are identified, inputted, and processed to enable a visual display of the target colour. Appearance characteristics of a target colour, such as texture, coarseness, may be identified in a further step. Flake appearance options are visually displayed images, which the user may superimpose with best match RGB data, in order to select the best flake appearance.

US 2003/0208345 relates to matching the appearance of a multicolour sample and to simulating the appearance of a multicolour surface. Reproducing the appearance of a sample multicolour surface comprises separating the multicolour surface into areas of different individual colours, identifying the individual colour of each area, translating said individual colours into colour values that correspond to those in a database of colours that have been produced, and searching the database for existing colours that are close matches for each colour in the multicolour sample. User input data may comprise colour component information and one or more of particle parameters, colour area fractions, texture, gloss, and other colour sample characteristics representing achievable multi-component coated finishes of known composition.

Known techniques for displaying effect coatings on electronic display devices involve superimposing a textured image that when judged by itself has the amount of texture corresponding to the measured texture value of the sample to be displayed, over a coloured image that when judged by itself has the colour properties corresponding to the measured colour values of the sample to be displayed. These techniques suffer from the fact that the perceived colour of an image changes when a textured image is superimposed on it. As a consequence, the perceived colour of the generated image of the effect coating deviates from the actual colour of the effect coating to be displayed.

This is undesirable, because an accurate display of an effect coating is much easier if the colour and the texture properties of the displayed image can be fixed independently.

A related disadvantage of the known technique is that when a user modifies the texture properties of a displayed textured image, also the perceived colour will change.

Additionally, when prior art techniques are used, visual judgment on the match between two displayed images of effect coatings is dependent on the distance between the user and the display device, due to the non-linear effect of texture on the perceived colour of the image.

The present invention seeks to alleviate the disadvantages described above.

Accordingly, the present invention provides a method of displaying an image of an effect coating having texture and colour properties on an electronic display device, using measured colour data and measured texture data as input to generate the image, wherein the textured image is displayed with visual colour properties which are maintained on a prescribed level independent of possible variations in texture properties.

The drawing displays one aspect of the invention whereby glint impression texture data and diffuse coarseness texture data are employed to generate a textured grayscale image, which, in turn, is used to generate a textured color image.

The method of the invention allows displaying images of effect coatings on electronic display devices, wherein the perceived colour of the effect coating is not influenced by the specific texture.

The method described in this application ensures that the displayed images maintain their prescribed colour properties, irrespective of the values for their texture properties. Prescribed colour properties refer to sets of parameters that fix the visual colour impression. Well-known examples of sets of colour parameters are the L* a* b* colour space coordinates defined by the Commission Internationale d'Eclairage (CIE), and the L*, u*, v* colour space coordinates, also defined by the CIE.

Besides colour, an effect coating film shows further visual properties. When effect pigments, such as for example aluminium flake pigments or pearlescent pigments, are used, the visual properties of a paint film are not uniform across the surface. This can include phenomena such as coarseness, glints, micro-brilliance, cloudiness, mottle, speckle, sparkle or glitter. In the following, texture is defined as the visible surface structure in the plane of the paint film depending on the size and organization of small constituent parts of a material. In this context, texture does not include roughness of the paint film but only the visual irregularities in the plane of the paint film. Also particles which are not directly observable by themselves, can contribute to the overall visual appearance of a paint film. Des-orienters are an example of such particles. Effect pigments are generally flakes tending to take a horizontal orientation in a cured film. To prevent this, and to obtain more variation in flake orientation, spherical particles are used, referred to as des-orienters. Using des-orienters in a metallic paint results in more glitter. Structures smaller than the resolution of the human eye contribute to colour, whereas larger structures generally also contribute to texture.

As mentioned above, the method of the invention uses measured colour and measured texture data as input to generate the image.

Colours can be measured with the aid of colour meters, such as spectrophotometers or tri-stimulus meters. US patent application US 2001/0036309 describes a method of measuring colour with the aid of a multi-angle spectrophotometer. U.S. Pat. No. 4,813,000 discloses measuring a selected colour with the aid of a tri-stimulus colour analyzer and using the measured chromaticity data. WO 01/25737 discloses how to measure colour with a digital imaging device such as a scanner or a digital camera.

Texture parameters can be measured using a digital imaging device, for example a digital camera having a CCD sensor. The texture parameter "coarseness" describes the visual surface roughness of a sample: a coating shows coarseness when it exhibits a clear pattern of dark and light areas, which is best recognizable under diffuse illumination conditions (the coarseness visible under such conditions is called "diffuse coarseness"). Not only the ratio between dark and light areas, which for a black and white image can be expressed in a gray value standard deviation, is of importance, but also the size of the areas. A coarseness scale has been designed with which an observer can visually inspect the effect coating and express the coarseness aspect as a number. Some effect coatings will have a small coarseness value, others a large coarseness value. In this way, the texture aspect "coarseness" of a coating can be visually determined in a quantitative way.

To extract coarseness, the following algorithm can be used:

Take a CCD image of N×N pixels. The gray value standard deviation GVSTD is determined at several scales X: At the smallest scale X=1 it is calculated per individual pixel. At the second smallest scale it is calculated over the average gray values of squares of 2×2 pixels (X=4). At the third smallest scale squares of 4×4 pixels are used, so X=16. This is repeated up to the maximum scale of N×N pixels (X=$N^2$).

The gray value standard deviation GVSTD can be described as a function of the scale X, using:

$$GVSTD = A + \frac{B}{X^C} \quad (1)$$

With GVSTD and X being known, the parameters A, B, and C can be calculated by fitting.

The A, B, and C parameters can be correlated to a visual coarseness value VC by:

$$VC = \alpha_1 + \alpha_2 * A + \alpha_3 * B + \alpha_4 * C \quad (2)$$

The values for the $\alpha_1$, $\alpha_2$, $\alpha_3$, and $\alpha_4$ have been predetermined in advance by comparison with a set of panels of representative car colours. These reference colours are judged by the eye and accorded a value according to a reference scale. Judging is done by a number of people and the accorded values are averaged per panel. For each of these reference colours, the measured VC should be equal to the value according to the reference scale for visual judgment. The parameters $\alpha_1$, $\alpha_2$, $\alpha_3$, and $\alpha_4$ are found by minimizing the difference between observed and measured values for all used panels in the set of representative car colours. To find equal values for the $\alpha_1$, $\alpha_2$, $\alpha_3$, and $\alpha_4$ parameters for all panels of the set of representative car colours, the square value of the difference between the reference scale value and the visual coarseness value VC is calculated for each panel. The sum of all these square values $\Sigma_{all\ panels}$ (visual judgment$_{panel\ i}$−VC$_{panel\ i}$)$^2$ is subsequently minimized, resulting in values for $\alpha_1$, $\alpha_2$, $\alpha_3$, and $\alpha_4$. With these parameters being known, the coarseness of any car paint film can be determined.

The aforementioned method of using the theoretical model (2) can be applied in general for any texture parameter for any observation and illumination condition for any particular model. This particular model can include any physical parameter (like particle size, flake composition, etc.), colour parameter (like CIE Lab parameters, etc.) or image parameters (like gray value standard deviation, etc.).

An alternative way to measure texture, in particular so-called micro-brilliance, with a digital imaging device and image analysis software is disclosed in US 2001/0036309, incorporated herein by reference.

The parameter "glints" is another texture parameter, which describes the perception of bright tiny light spots on the surface of an effect coating under directional illumination conditions that switch on and off when you change the viewing angle. Glint is best observed in direct sunlight, i.e. with a cloudless sky, from less than one meter. Even when the observation conditions are the same, some effect coatings show many bright glints, whereas other effect coatings show few or even no glints at all. A glint scale has been designed with which an observer can visually inspect the effect coating and express the glints aspect as a number that is referred to as "glint impression". Some effect coatings will have a small glints value, others a large glints value. In this way, the texture aspect "glint" of a coating can be visually determined in a quantitative way.

The texture parameter "glints" can be described more specifically by making the distinction between glint intensity and glint size. Glint intensity is the light intensity or light intensity distribution of the bright tiny light spots. Glint size is the area or area distribution of the spots.

A second way to make a further distinction between glints is by their colour or colour distribution.

A glint is visible only in a given range of mutual orientations of illumination direction, observation direction, and sample orientation. As a consequence, a third way to characterize glints is to determine the range of illumination angles (or the distribution thereof) for which a glint is visible to the human eye, given a certain observation angle and sample orientation. Similarly, the range of observation angles (or the distribution thereof) for which a glint is visible to the human eye can be used given a fixed illumination angle and sample orientation, or the range of sample orientations (or the distribution thereof) for which a glint is visible to the human eye can be used given a fixed observation angle and a fixed illumination angle.

An example of a commercially available instrument to measure texture parameters is the BYK-mac® from BYK-Gardner. With this instrument, several texture parameters can be measured for different illumination conditions, such as different degrees of directionality of the light source and different illumination angles and detection angles. Utilizing data from texture measurements from more than one illumination angle and/or detection angle, and using that data to display images that account for the variation in texture properties when these angles are varied, are another particular optional advantage of the present invention as compared to prior art such as disclosed in International patent application WO 2008/121358.

The electronic display device on which the image of an effect coating is displayed can be a computer monitor, a projector, a TV screen, a personal digital assistant (PDA) device, a cell phone, a smart phone that combines PDA and cell phone, a flexible thin film display, or any other devices that can display information or images based on digital signals. The display device can also be a printing device that prints, based on digital signals, information or image onto papers, plastics, textiles, or any other surfaces that are suitable for printing the information or images onto. The display device can also be a dual functional display/data input device, such as a touch screen.

In one particular embodiment the method of the invention comprises a first step a) of generating a grayscale image with prescribed texture properties, in which the texture property can be diffuse coarseness, or glint impression, or any combination of these. In a further step b) the generated grayscale textured image is converted into a textured image with prescribed colour properties.

In a still further embodiment, the displayed image takes into account the viewer's distance to the displayed effect coating. This can be achieved by a method wherein in step a) the diffuse coarseness image is resized by means of an interpolating resize algorithm, the glint impression image is resized by a non-interpolating resize algorithm, and subsequently the resized diffuse coarseness image and glint impression images are combined to a resized grayscale image with prescribed texture properties, and wherein the degree of resizing depends on the viewer's distance to the displayed coatings.

In the first step, two grayscale images with prescribed texture properties are generated by an algorithm that puts patches of a certain size and a certain gray level at a number of randomly generated positions in the images. One image is made to simulate the diffuse coarseness aspects, whereas the second image is made to simulate the glint impression aspects. In a subsequent stage, both aspects are combined into one final image, optionally taking into account the distance between viewer and display device.

Both images are generated by a core algorithm, described below, that utilizes input parameters size, gray level, count, and sparkler. For the first image, the size, gray level, count factor, and sparkler factor are chosen by functions that depend only on the measured diffuse coarseness value:

$$\begin{bmatrix} \text{size} \\ \text{gray level} \\ \text{count} \\ \text{sparkler} \end{bmatrix} = \begin{bmatrix} f(dc) \\ g(dc) \\ h(dc) \\ k(dc) \end{bmatrix} \quad (3)$$

where f(dc), g(dc), h(dc) and k(dc) are described as a function of diffuse coarseness dc:

$$f(dc) = A_f + B_f \cdot dc^{C_f}$$

$$g(dc) = A_g + B_g \cdot dc^{C_g}$$

$$h(dc) = A_h + B_k \cdot dc^{C_k}$$

$$k(dc) = A_k + B_k \cdot dc^{C_k} \quad (4)$$

With dc known for a representative set of car colours, either from visual judgements or by measurements, the core algorithm is able to simulate images that were captured with a digital camera under well defined illumination and detection conditions for that set of panels. To make the simulated images resemble the measured images, the parameters $A_f$, $B_f$ through $C_k$ must be optimized. In this process, the simulated images are said to be optimal when a number of carefully selected statistical measures of their histogram match those of the measured set. Examples of such statistical measures are the median value, the average, and percentile values for 10, 20, . . . up to 100 percent.

To find equal values for the parameters $A_f$, $B_f$ through $C_k$ for all panels of the set of representative car colours, the square value of the difference between these statistical measures is calculated for each of the measured and simulated images. The sum of the squared differences is subsequently minimized, resulting in an optimized value for each parameter $A_f$, $B_f$ through $C_k$. With these parameter values, the diffuse coarseness of any car paint film can be accurately simulated in a digital image.

For the second image, the size, gray level, count factor, and sparkler factor are chosen by functions that depend only on the measured glint impression value:

$$\begin{bmatrix} \text{size} \\ \text{gray level} \\ \text{count} \\ \text{sparkler} \end{bmatrix} = \begin{bmatrix} m(gi) \\ n(gi) \\ p(gi) \\ q(gi) \end{bmatrix} \quad (5)$$

where the functions m, n, p, and q are similar to the functions f, g, h, and k introduced in equation (4), but further transformed using a simplified Fermi-Dirac distribution function:

$$m(gi) = 1 + 100/(1 + \exp[A_f + B_f \cdot gi^{C_f}])$$

$$m(gi) = 1 + 100/(1 + \exp[A_g + B_g \cdot gi^{C_g}])$$

$$m(gi) = 1 + 100/(1 + \exp[A_h + B_h \cdot gi^{C_h}])$$

$$m(gi) = 1 + 100/(1 + \exp[A_k + B_k \cdot gi^{C_k}]) \quad (6)$$

Similar to the previous case, the parameters $A_f$, $B_f$ through $C_k$ must be optimized to generate images that resemble the glint impression of the measured set of representative car colours; again in such a way that one set of parameters yields images resembling a panel with the given glint impression value.

Here, a digital image is regarded as a two-dimensional array of pixel values. The core algorithm starts with an array of the correct size, or slightly overdimensioned size, filled with zeroes.

In a next step, which is repeated count×array$_{13}$ size times, the algorithm increases the values at a random small rectangular section in the image. For the given values for the parameters in equations (3) and (5), these increments have the given size and a pattern that depends on the given size. The pattern may be a point-spread-function, or a generated or measured secondary image, possibly depending on more parameters. After each increment, the pattern can multiplied by the sparkler value.

After the addition of the given gray level value, the resulting array is normalized to contain no values exceeding unity.

In the further step, the grayscale images with specified glint impression or specified diffuse coarseness value generated with the previously described algorithm are combined to produce one digital image with texture and colour properties corresponding to specified illumination conditions, and for which the perceived colour is equal to a prescribed colour.

For a specified combination of illumination angle and observation angle, abbreviated by the term geometry, the generated grayscale image with specified glint impression is converted in this step to a coloured image with the same specified value for glint impression and with a perceived colour equal to the prescribed colour. Using methods well known to those skilled in the art, a non-textured coloured digital image with the prescribed colour properties for the specified geometry is generated, based on reflection measurements from e.g. a spectrophotometer, and in which the spectral power distribution of the light source is taken into account. We will write Rm, Gm, and Bm for the so-called Red, Green, and Blue values of this image, g for the geometry of interest, and x, y for the coordinates of a pixel in a digital image.

The grayscale image with glint impression as specified for a certain geometry g has pixel values that are denoted here as GI, which are obviously equal for the red, green, and blue channels. These values vary for different pixels x, y. The values averaged over all pixel coordinates will be denoted as GIavg. Any unintended colour difference between generated grayscale images is accounted for by subtracting the average value.

Also, the resulting pixel values are limited to a fixed range of values, which is here taken to be normalized to the range from zero to unity. In this way, an intermediate digital image is generated with pixel values Rsa, Gsa, and Bsa for the red, green, and blue channels, respectively.

$$Rsa(g,x,y)=\max(0,\min(1,Rm(g)+GI(g,x,y)-GIavg(g)))$$

$$Gsa(g,x,y)=\max(0,\min(1,Gm(g)+GI(g,x,y)-GIavg(g)))$$

$$Bsa(g,x,y)=\max(0,\min(1,Bm(g)+GI(g,x,y)-GIavg(g)))$$

This method ensures that for the resulting intermediate image not only the texture aspect glint impression is equal to the specified value, but also that its perceived colour agrees with the reflection values measured by the spectrophotometer. This is accomplished partly by the terms correcting for the average values of the grayscale textured images. However, it also results because the core algorithm for producing the grayscale textured images is calibrated by a visual comparison of the generated images with a series of grayscale images from so-called anchor panels. These anchor panels are coating samples that are formulated by colour experts, who are given the task of producing a set of gray coating samples that show no difference in colour, but that do show a gradual change in texture when observed under appropriate, well-defined illumination and observation conditions.

In this way, a series of anchor panels is produced that gradually varies in diffuse coarseness when observed under diffuse illumination. A different series of anchor panels is produced that gradually varies in glint impression when observed under directional illumination. With a digital camera at a specified detection angle, grayscale images are captured from the anchor panels. This results in one series of grayscale images with a range of known values of diffuse coarseness, and another series of grayscale images with a range of known values for glint impression. By visual comparison of the grayscale images generated by the core algorithm on the one hand and grayscale images of the anchor panels on the other, the core algorithm is guaranteed to provide achromatic images with specified texture properties.

In a similar way, another intermediate digital image with pixel values Rsd(x, y) is generated in which the texture aspect of diffuse coarseness is taken into account, based on the generated grayscale digital image DC(x, y) and its average value DCavg.

$$Rsd(x,y)=\max(0,\min(1,Rmd+DC(x,y)-DCavg))$$

$$Gsd(x,y)=\max(0,\min(1,Gmd+DC(x,y)-DCavg))$$

$$Bsd(x,y)=\max(0,\min(1,Bmd+DC(x,y)-DCavg))$$

In this last expression, the parameters Rmd, Gmd, Bmd refer to the values for the red, green, and blue channels calculated for a non-textured coloured image that would result if the sample were diffusely illuminated. The values of the parameters Rmd, Gmd, Bmd are best measured with a spectrophotometer with diffuse lighting, or alternatively they may be calculated based on a combination of the reflection values measured for a number of specified geometries under directional, non-diffuse lighting.

Based on the two intermediate coloured digital images, which show the specified texture aspect of glint impression (applicable to directional lighting conditions) and diffuse coarseness (applicable to diffuse lighting conditions), respectively, the final coloured digital image showing the resulting texture under the specified lighting conditions is constructed.

This is realized by introducing an optional parameter v specifying the viewer's distance to the displayed coatings, and a parameter d specifying the fraction of diffuse light in the light conditions that are valid at the place where the coatings are inspected. A value v=1 then refers to an unscaled texture, v=2 refers to normal viewing distance ($\approx$60 cm), and beyond. Prior to combining the two, the diffuse coarseness image is to be scaled using an interpolating resize algorithm such as "bilinear resize", whereas the glints impression image is to be scaled using a non-interpolating resize algorithm such as "nearest neighbour". This distinction ensures that the respective diffuse and directional nature of the images is preserved. Further, a parameter d is introduced, specifying the fraction of diffuse light in the light conditions that are valid at the place where the coatings are inspected. A value d=1 then refers to purely diffuse lighting, d=0 refers to purely directional light, and intermediate values refer to corresponding intermediate illumination conditions.

$$R(g,x,y)=\max(0,\min(1,Rsd(x,y)*d+Rsa(g,x,y)*(1-d))$$

$$G(g,x,y)=\max(0,\min(1,Gsd(x,y)*d+Gsa(g,x,y)*(1-d))$$

$$B(g,x,y)=\max(0,\min(1,Bsd(x,y)*d+Bsa(g,x,y)*(1-d))$$

In order to limit the number of time-consuming calculations of textured grayscale images, a representative set of grayscale images with a number of specified values for diffuse coarseness or glint impression is calculated and stored. Using stored textured images could lead to visible artifacts when simulated images using the same textures are shown next to each other. In that case, the user could become aware that a limited number of stored pre-calculated images is used and thereby attention would be distracted from the images. This is prevented by applying randomly mirroring and/or rotation operations to sections of the images State of the art spectrophotometers provide reflection curves for typically six to twenty different geometries g. Images or parts of images referring to geometries g that are not equal to one of the geometries available in the spectrophotometer can be generated by using interpolation techniques, such as linear interpolation, quadratic interpolation, and spline functions.

For geometries close to the specular angle that are not measured by conventional spectrophotometers, the generated image obtains an even better likeness to physical samples with coatings if gloss is accounted for. This may be realized by adding to the pixel values a white reflection of the light source, representing the gloss level of the physical sample (for example, typically four percent for high gloss coatings), smoothed out by a function that distributes the gloss over geometries around the specular angle to account for surface irregularities and for blur in the projection of the light source.

The visual properties of effect coatings having texture and colour properties generally depend on the illumination and observation conditions.

Therefore, in one embodiment, texture data measured under at least two different illumination and/or observation conditions are used as input to generate the image. For a better impression of the overall visual properties of a specific effect coating, it is also preferred to display an image of the effect coating on the electronic display device under at least two different illumination and/or observation conditions.

In one embodiment, at least two different illumination and/or observation conditions are implemented by light sources having a different spectral output. In a further embodiment, at least two different illumination and/or observation conditions are implemented by light having different degrees of directionality, for example entirely diffuse light, and light having a high degree of directionality. In a further embodiment, at least two different illumination and/or observation conditions are implemented by different illumination angles and/or different observation angles. It is also possible to combine one or more of the embodiments which implement different illumination and/or observation conditions.

When observing an object, its surface is viewed under a range of illumination angles and/or viewing angles with respect to the local surface. Therefore, in a further embodiment, each displayed image represents a range of illumination angles and/or observation angles. This makes it possible to represent any curved object under many illumination and/or viewing angles. The dependence of both colour and texture properties on these angles is accounted for. It is also possible to display images under ranges of illumination and/or observation angles that do not correspond to realistic scenes, but that may be useful for emphasizing the characteristic dependence of colour and/or texture properties on these angles.

It also possible to display two or more images of effect coatings simultaneously. Simultaneous display of effect coatings is particularly useful to compare the visual properties of different effect coatings.

In a further embodiment, the displayed image is linked to a corresponding coating recipe and changes of texture and colour properties upon a modification of the coating recipe are visualized.

The method of displaying effect coatings of the invention is highly suitable for selecting candidate coatings for matching a target coating. In one embodiment, the images of at least two effect coatings displayed simultaneously include the image of a target coating to be matched and the image of a candidate coating which potentially matches the visual properties of the target coating.

Therefore, in one aspect, the method comprises the steps of
  a) visually comparing the degree of matching of texture and colour properties of a target coating on a substrate having texture and colour properties with two or more physical samples of candidate coatings,
  b) selecting the physical sample of the candidate coating having the best match with the target coating,
  c) visually determining the deviations in texture and colour between the target coating and the physical sample of the candidate coating selected in step b)
  d) displaying an image of the physical sample of the candidate coating selected in step b) and at least one alternative potential candidate coating, using a method as described above, and
  e) selecting, based on the deviations determined in step c), the best matching candidate coating from the displayed images.

This method does not require measuring the texture and colour properties of the target coating and displaying an image thereof.

In another aspect, the invention relates to a method of selecting a candidate coating having texture and colour properties matching the texture and colour properties of a target coating on an article, comprising the steps of
  a) displaying an image of the target coating and an image of at least one candidate coating on an electronic display device using a method as described above,
  b) establishing the degree of matching of colour and texture properties between the target coating and at least one candidate coating by visually comparing the images displayed in step a), and
  c) selecting a candidate coating that has an acceptable degree of matching.

In a preferred embodiment of the method of selecting a candidate coating, the images of two or more candidate coatings are displayed on the electronic display device. The two or more images of candidate coatings may be displayed simultaneously or consecutively.

When the visible differences between images of a target coating to be matched and one or more candidate coatings are small, it may be difficult to select the candidate coating which has the best degree of matching.

Therefore, in a further embodiment, differences in the texture and/or colour properties of the target coating and at least one candidate coating are amplified in the displayed images and/or in a separate image showing the amplified colour difference. This makes it easier to select from a number of candidate coatings the one which has the best degree of matching with the target coating. In a further embodiment, the images of the target coating and at least one candidate coating are displayed for a range of illumination angles and/or observation angles, and the range of displayed illumination angles and/or observation angles includes those angles under which the difference in texture and/or colour properties between the target coating and at least one candidate coating reaches a maximum. In a further embodiment, the range of illumination angles and/or observation angles used in the displayed image is not representative for ranges of angles realized when realistic physical objects are observed, but is selected to emphasize differences in texture and/or colour properties.

In one embodiment, the candidate images are supplemented by textual or graphical indications of the accuracy of the match with respect to colour properties and/or the accuracy of the match with respect to texture properties and/or the tintability of the candidate. In this way, the user is aided in finding the best candidate for a match. If the best candidate for a match is not good enough, the user has to change the colour recipe of the best candidate, a process known as correcting or tinting.

The process of correcting/tinting colour recipes that were obtained from a database is aided in a further embodiment, by displaying the colour and texture properties of one or more candidate coatings and visualizing how those properties would change after one or more proposed modifications of the colour recipes. The proposed modifications of the colour recipes can be the result of calculations.

In a further embodiment, the proposed modifications of the colour recipes consist of prescribed slight changes of the recipe.

In one embodiment, the measured colour data and measured texture data used as input to generate the textured image with prescribed colour properties, are stored in and retrieved from a database containing measured colour data and measured texture data of effect coatings. The database may be implemented on a local electronic data storage device. Alternatively, the database may be implemented on a remote storage device which is accessible via a data communication line, for example the internet.

In a further aspect, the invention relates to a system for carrying out the method, more in particular a system for displaying an image of an effect coating having texture and colour properties on an electronic display device, wherein the system comprises an electronic display device under the control of a data processing unit which is configured to use measured colour data and measured texture data as input to generate a texture image with visual colour properties which are maintained on a prescribed level independent of possible variations in texture properties.

The invention claimed is:

1. A method of displaying an image of an effect coating having texture and color properties on an electronic display device under the control of a data processing unit, the method comprising generating the image by using measured color data and measured texture data as input for the data processing unit, and displaying the textured image with visual color properties which are maintained on a prescribed level independent of possible variations in texture properties, such that the perceived color is not influenced by the specific texture, wherein the method comprises,
   a) first generating a grayscale image with prescribed texture properties, wherein the texture properties are selected from the group consisting of diffuse coarseness, glint impression, or a combination of these, and
   b) second, converting the generated grayscale textured image into a textured image with prescribed color properties,
   wherein in a) the texture properties are a combination of diffuse coarseness and glint impression, and the diffuse coarseness image is resized by means of an interpolating resize algorithm, the glint impression image is resized by a non-interpolating resize algorithm, and subsequently the resized diffuse coarseness image and glint impression image are combined to a resized grayscale image with prescribed texture properties, and wherein the degree of resizing depends on the viewer's distance to the displayed effect coating.

2. The method according to claim 1, wherein texture data measured under at least two different conditions are used as input to generate the grayscale image with prescribed texture properties, wherein the at least two different conditions are selected from the group consisting of illumination conditions, observations conditions, and combinations thereof.

3. The method according to claim 2, wherein the at least two different illumination conditions are implemented by light sources having different spectral output.

4. The method according to claim 3, wherein the at least two different illumination conditions are implemented by light having different degrees of directionality.

5. The method according to claim 2, wherein the at least two different illumination conditions are implemented by light having different degrees of directionality.

6. The method according to claim 1, wherein the image is displayed under at least two different conditions, wherein the at least two different conditions are selected from the group consisting of illumination conditions, observations conditions, and combinations thereof.

7. A method of displaying an image of an effect coating having texture and color properties on an electronic display device, comprising
   a) visually comparing the degree of matching of texture and color properties of a target coating on a substrate having texture and color properties with two or more physical samples of candidate coatings,
   b) selecting the physical sample of the candidate coating having the best match with the target coating,
   c) visually determining the deviations in texture and color between the target coating and the physical sample of the candidate coating selected in b),
   d) displaying an image of the physical sample of the candidate coating selected in b) and at least one alternative potential candidate coating, using the method according to claim 1,
   e) selecting, based on the deviations determined in c), the best matching candidate coating from the displayed images.

8. The method according to claim 1, wherein the displayed image is linked to a corresponding coating recipe and wherein upon a modification of the coating recipe, changes of texture and color properties are visualized.

9. The method according to claim 1, wherein images of at least two effect coatings are displayed simultaneously.

10. The method according to claim 9, wherein the images of at least two effect coatings include the image of a target coating to be matched and the image of a candidate coating which potentially matches the visual properties of the target coating.

11. A method of selecting a candidate coating having texture and color properties matching the texture and color properties of a target coating on an article, comprising
   a) displaying an image of the target coating and an image of at least one candidate coating on an electronic display device using the method according to claim 1,
   b) establishing the degree of matching of color and texture properties between the target coating and at least one candidate coating by visually comparing the images displayed in a), and
   c) selecting a candidate coating that has an acceptable degree of matching.

12. The method according to claim 11, wherein the image of the candidate coating is supplemented by textual or graphical indications of the degree of matching between the target coating and the candidate coating.

13. The method according to claim 11, wherein the images of at least two candidate coatings are displayed simultaneously on the electronic display device.

14. The method according to claim 11, wherein differences in the properties of the target coating and at least one candidate coating are amplified in the displayed images, wherein the differences in properties are selected from the group consisting of differences in texture, differences in color, and combinations thereof.

15. The method according to claim 11, wherein the images of the target coating and at least one candidate coating are displayed for a range of angles, wherein the range of angles are selected from the group consisting of illumination angles, observation angles, and combinations thereof, and wherein the range of displayed angles includes those angles under which the difference in properties between the target coating and at least one candidate coating reaches a maximum, wherein the properties are selected from the group consisting of texture, color, and combinations thereof.

16. A system for displaying an image of an effect coating having texture and color properties on an electronic display device, the system comprising an electronic display device under the control of a data processing unit which is configured to use measured color data and measured texture data as input to generate a textured image with visual color properties which are maintained on a prescribed level independent of possible variations in texture properties, such that the perceived color is not influenced by the specific texture, wherein the system is further configured to, a) generate a grayscale image with prescribed texture properties, wherein the texture properties are selected from the group consisting of diffuse coarseness, glint impression, or a combination of these, and b) convert the generated grayscale textured image into a textured image with prescribed color properties, wherein the texture properties in a) are a combination of diffuse coarseness and glint impression, and the diffuse coarseness image is resized by means of an interpolating resize algorithm, the glint impression image is resized by a non-interpolating resize algorithm, and subsequently the resized diffuse coarseness image and glint impression image are combined to a resized grayscale image with prescribed texture properties, and wherein the degree of resizing depends on the viewer's distance to the displayed effect coating.

17. The method according to claim 12, wherein the images of at least two candidate coatings are displayed simultaneously on the electronic display device.

18. The method according to claim 14, wherein the images of the target coating and at least one candidate coating are displayed for a range of angles, wherein the range of angles are selected from the group consisting of illumination angles, observation angles, and combinations thereof, and wherein the range of displayed angles includes those angles under which the difference in properties between the target coating and at least one candidate coating reaches a maximum, wherein the properties are selected from the group consisting of texture, color, and combinations thereof.

* * * * *